US008834465B2

(12) United States Patent
Ramstein et al.

(10) Patent No.: US 8,834,465 B2
(45) Date of Patent: Sep. 16, 2014

(54) MODULAR TOOL WITH SIGNAL FEEDBACK

(75) Inventors: Christophe Ramstein, San Francisco, CA (US); Christopher J. Ullrich, Ventura, CA (US); Anne DeGheest, Los Altos Hills, CA (US)

(73) Assignee: Immersion Corporation, San Jose, CA (US)

( * ) Notice: Subject to any disclaimer, the term of this patent is extended or adjusted under 35 U.S.C. 154(b) by 1159 days.

(21) Appl. No.: 12/173,177

(22) Filed: Jul. 15, 2008

(65) Prior Publication Data
US 2010/0016855 A1   Jan. 21, 2010

(51) Int. Cl.
*A61B 18/14*  (2006.01)
*A61B 1/00*  (2006.01)
*A61B 17/29*  (2006.01)
*A61B 19/00*  (2006.01)
*A61B 18/00*  (2006.01)
*A61B 17/00*  (2006.01)

(52) U.S. Cl.
CPC ................. *A61B 17/29* (2013.01); *A61B 19/44* (2013.01); *A61B 2018/00178* (2013.01); *A61B 2017/00464* (2013.01); *A61B 2562/225* (2013.01); *A61B 1/00105* (2013.01); *A61B 2017/00022* (2013.01); *A61B 18/1442* (2013.01); *A61B 2017/00482* (2013.01); *A61B 18/14* (2013.01)
USPC .......................................................... 606/46

(58) Field of Classification Search
CPC ........... A61B 1/00105; A61B 1/00121; A61B 1/00124
USPC .......... 606/48, 52, 46; 607/98–100, 112, 115; 600/128, 130
See application file for complete search history.

(56) References Cited

U.S. PATENT DOCUMENTS

| 5,578,052 | A | * | 11/1996 | Koros et al. ................... 606/174 |
| 5,766,167 | A | * | 6/1998 | Eggers et al. ................... 606/46 |
| 7,090,637 | B2 | | 8/2006 | Danitz et al. |
| 7,326,202 | B2 | | 2/2008 | McGaffigan |
| 2003/0045888 | A1 | | 3/2003 | Brock et al. |
| 2003/0191464 | A1 | * | 10/2003 | Kidooka .......................... 606/45 |
| 2004/0153124 | A1 | * | 8/2004 | Whitman ........................ 606/219 |
| 2005/0113821 | A1 | | 5/2005 | Pendekanti et al. |
| 2006/0200216 | A1 | * | 9/2006 | Calzada et al. ............... 607/116 |
| 2007/0023477 | A1 | * | 2/2007 | Whitman et al. ........... 227/175.1 |

FOREIGN PATENT DOCUMENTS

WO    WO 01/62164    8/2001

OTHER PUBLICATIONS

PCT/US2009/043546—International Search Report and Written Opinion.
Stryker®, "Reliability for all Laparoscopic Procedures", Literature Number: 1000-900-269 Rev. D, Apr. 2004.

* cited by examiner

*Primary Examiner* — Michael Peffley
*Assistant Examiner* — Thomas Giuliani
(74) *Attorney, Agent, or Firm* — Medler Ferro PLLC

(57) ABSTRACT

Implementations of modular tools and methods of operating modular tools are described in the present disclosure. A modular tool according to one of several possible embodiments comprises a handle portion and a distal portion. The handle portion is configured to be manipulated by a user. The distal portion is configured to be attached to the handle portion, but is further configured to be removable from the handle portion by the user. Manipulation of the handle portion causes movement of one or more components of the distal portion. The distal portion is further configured to sense one or more parameters and transmit the sensed parameters to the handle portion.

17 Claims, 3 Drawing Sheets

MODULAR TOOL WITH SIGNAL FEEDBACK

TECHNICAL FIELD

The embodiments of the present disclosure generally relate to modular tools and more particularly relate to mechanical and electrical communication between different portions of a modular tool.

BACKGROUND

In the field of surgery, open surgical procedures involve creating a relatively large incision in the abdomen of a patient allowing the surgeon to access various organs. On the other hand, laparoscopic surgical procedures involve accessing organs through one or more small incisions, which makes these procedures less invasive than open surgery. Since laparoscopic procedures are less invasive, hospitalization times are typically reduced, patients require less therapy, patients experience less pain, scarring is reduced, and the likelihood of complications is reduced.

In laparoscopic procedures, a miniature camera can be introduced into the body of the patient through an incision. The camera transmits images to a video monitor enabling the surgeon to view the patient's organs for diagnosing and treating the patient as needed. The surgeon can also introduce surgical instruments and auxiliary devices, such as irrigation and drainage devices, through one or more additional small incisions.

One challenge regarding the use of surgical tools is sterilization, since surgical tools must be sterile in order to be used in an operating context. One school of thought is to always use disposable tools, which are used once and then discarded. Although this may seem wasteful, there are some benefits to this methodology. For instance, a surgeon has the assurance that new tools will be sterile. New tools are at the beginning of their effective life and are therefore more reliable. Among other benefits, there can be reduction in a hospital's liability since the transfer of pathogens from one patient to another is essentially eliminated.

Another school of thought is that many tools can be sterilized after use and should therefore be reused. Particularly, this methodology can be beneficial with respect to more expensive tools or those that are very reliable. By sterilizing tools, waste can be minimized. Some tools can be autoclaved, which is a sterilizing procedure that involves exposing the tools to high pressure and high temperature steam, which kills any biological matter on the tools. However, since only certain types of tools, such as stainless steel tools, can be autoclaved, other tools should be sterilized using other methods. For example, tools that contain parts that are sensitive to heat or moisture, such as electronic circuitry, can often be sterilized using other sterilization procedures. A difficulty with sterilization methodologies, however, is that a hospital will be required to dedicate a facility within the hospital for sterilization practices and must follow an effective program to ensure proper enforcement of sterilization procedures.

Based on the advantages and disadvantages of the two schools of thought as mentioned above, there is a trade-off between the concepts of using disposable tools and using tools that can be sterilized after use. An intermediate position can be taken between disposable tools and reusable tools, referred to herein as "reposable" tools. Reposable tools are designed such that a portion of the tool is disposable and a portion of the tool is reusable.

SUMMARY

The present disclosure describes embodiments of modular tools and further describes methods of operating modular tools. In one embodiment, among others, a modular tool comprises a handle portion and a distal portion, where the distal portion is configured to be attached to the handle portion. The handle portion is configured to be manipulated by a user. Although the distal portion can be attached to the handle portion, it is further configured to be removable from the handle portion by the user. Manipulation of the handle portion causes movement of one or more components of the distal portion. The distal portion is further configured to sense one or more parameters and transmit the sensed parameters to the handle portion.

Other features, advantages, and implementations of the present disclosure, not expressly disclosed herein, will be apparent to one of ordinary skill in the art upon examination of the following detailed description and accompanying drawings. It is intended that such implied implementations of the present disclosure be included herein.

BRIEF DESCRIPTION OF THE DRAWINGS

The components of the following figures are illustrated to emphasize the general principles of the present disclosure and are not necessarily drawn to scale. Reference characters designating corresponding components are repeated as necessary throughout the figures for the sake of consistency and clarity.

DETAILED DESCRIPTION

Figure 1:
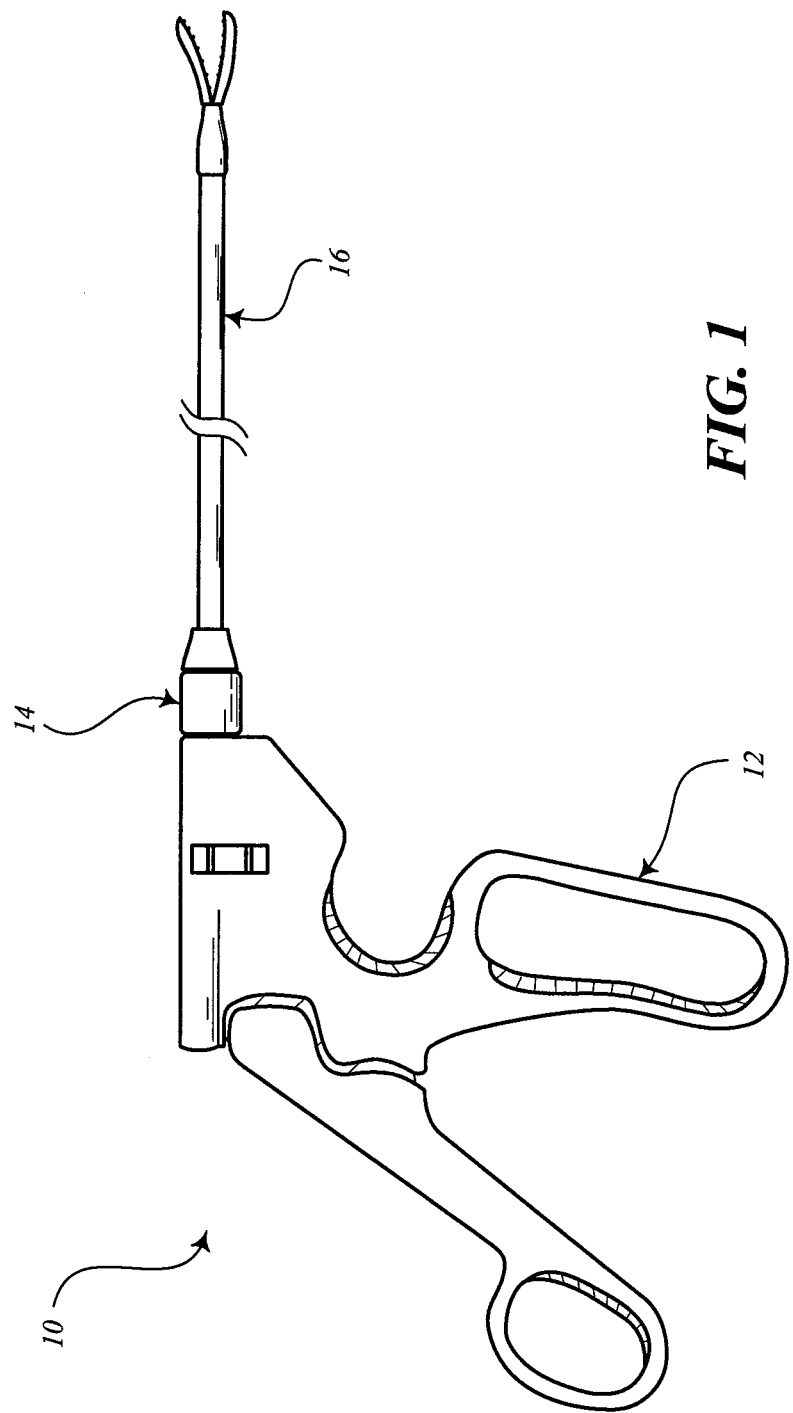
FIG. 1 is a diagram illustrating a modular tool according to one embodiment.

A surgeon performing a laparoscopic procedure is usually unable to directly view the interaction between the surgical instruments and the tissues and organs of the patient. However, by inserting image capturing devices to observe the distal ends of the tools, a surgeon can rely on visual feedback to identify the anatomy of the patient. To achieve a greater chance of success in laparoscopic procedures, the surgeon should manipulate the surgical tools with dexterity and sensitivity. In some cases, the distal end of a tool may include sensors to provide multimodal (i.e. visual, auditory, and/or tactile) feedback to the surgeon. With this multimodal feedback, a surgeon can better monitor forces applied by the tools to reduce injuries and trauma to the tissues and organs, thereby reducing complications associated with laparoscopic procedures.

Another aspect that correlates to the success of surgical procedures is proper sterilization of instruments. With respect to reposable tools, one or more portions of a reposable tool can be sterilized after use and reused while one or more other portions of the tool can be discarded. Reposable tools therefore include different portions that can be assembled together, used as an assembled tool, and then disconnected from each other. The reusable portions are sterilized for further use and the disposable portions are thrown out. One of the many advantages of reposable tools is that the different portions can be assembled in any number of possible combinations. For example, depending on a surgeon's preferences, certain handle portions may be selected and can be used with certain distal portions that contain elements designed to act upon the tissues and organs. Therefore, a variety of ends or tips can be connected to a variety of handles to create diverse combinations of modular tools.

For the portions of the modular tools that can be sterilized for later use, any suitable type of sterilization procedure can be used, depending on the particular design of the portion and the materials or components contained in the portion. For example, a handle portion may include electronic circuitry that may be sensitive to heat and/or moisture. Therefore, hot steam sterilization might not be an acceptable practice in this case, unless the sensitive portions are covered or sealed with a suitable protective device. Other sterilization techniques may also be used, such exposing the reusable portions to ethylene oxide, using a hydrogen peroxide gas plasma technology, gamma irradiation, electron-beam irradiation, etc.

The embodiments of the present disclosure describe distinct portions of modular tools that can be assembled together to form a usable tool. In some embodiments, an interface portion or adapter is connected intermediately between a handle portion and a distal portion. Whether designed with or without the interface portion, the embodiments herein allow communication between the handle portion and the distal portion. Specifically, the communication is in the form of mechanical translation from the handle portion to the one or more components of the distal portion. In this way, the surgeon can manipulate the handle in such a way to cause the distal portion to perform specific functions on the tissues and organs. In addition, communication described herein includes electrical communication between the handle portion and the distal portion. For example, electrical communication may include providing high voltage from the handle portion to the distal portion, such as for cauterization. Electrical communication may also include providing low voltage, such as approximately 5V, from the handle portion to the distal portion. This voltage can be used to power the sensing elements of the distal portion as needed. Furthermore, electrical communication includes the transmission of sensor signals from the distal portion to the handle portion representing sensed parameters at the distal portion.

Although many of the examples described herein relate to modular surgical tools and more specifically modular laparoscopic surgical tools, it should be understood that the teachings of the present disclosure also encompass any suitable type of modular hand tools. Other implementations and advantages will become apparent to one of ordinary skill in the art from an understanding of the present disclosure.

FIG. 1 is a diagram illustrating an embodiment of a modular tool 10 having at least two portions. In particular, modular tool 10 is shown in FIG. 1 as a modular laparoscopic surgical tool. In other embodiments, however, modular tool 10 may be configured as any type of modular hand tool for performing any type of functions and furthermore is designed with suitable means for mechanically translating forces and electrically communicating signals between a handle portion and a distal portion.

In the embodiment of FIG. 1, modular tool 10 includes a handle portion 12, an adapter or interface portion 14, and a distal portion 16. In some embodiments, interface portion 14 may be omitted such that handle portion 12 can be connected directly to distal portion 16. In other embodiments, the elements of interface portion 14, as described in more detail below, may be incorporated partially or entirely into handle portion 12 and/or distal portion 16. Handle portion 12, interface portion 14, and distal portion 16 can be attached together to form modular tool 10. When attached, modular tool 10 can be used as designed. After use, handle portion 12, interface portion 14, and/or distal portion 16 can be removed or disconnected from the other portions. In the case where one portion, e.g., distal portion 16, is a disposable item, this portion can be removed from modular tool 10 and discarded.

Modular tool 10 is designed such that handle portion 12 can be selected from a plurality of handle portions. Also, distal portion 16 can be selected from a plurality of distal portions. With compatible interconnections between the different handle portions and distal portions, a user can connect the portions in any number of combinations, depending on the particular preferences or needs of the user. Interface portion 14 may be used to connect different families or classes of handle portions with different families or classes of distal portions. In some embodiments, however, handle portions and distal portions can be designed such that they can be connected to each other using a single interface portion 14 having a universal design for all types of handle portions and distal portions.

When a user physically manipulates handle portion 12, mechanical forces applied to handle portion 12 are translated to cause movement of one or more components of distal portion 16. As needed, this mechanical translation is communicated through or by way of interface portion 14. Furthermore, parameters that are sensed at distal portion 16 can be electrically transmitted back to handle portion 12. The types of parameters that can be sensed by distal portion 16 may include, for example, optical images, pressure, force, temperature, biological information, flexibility, tissue identification, tip resistance, trajectory information, Doppler information, active or passive piezoelectric transducer ("PZT") information, polyvinylidene fluoride ("PVDF") sensor information, strain gauge measurements, ultrasound, etc.

Handle portion 12 may include certain processing elements as needed, such as, for example, filters, analyzing circuitry, amplifiers, etc. Also, handle portion 12 may include a display device for displaying the sensed parameters. In addition, handle portion 12 may include a haptic actuator, such as, for example, a vibrotactile actuator, kinesthetic actuator, deformable surface actuator, electromagnetic actuator, eccentric rotating mass ("ERM"), linear resonant actuator ("LRA"), "smart material", piezoelectric material, electroactive polymer, shape memory alloys, etc. With a haptic actuator, handle portion 12 can invoke a haptic effect to the hands of the user. Also, handle portion 12 can include handle mounted sensors, such as, for example, user grip force sensors, gripper angle sensors, etc.

In some embodiments, handle portion 12 may include a wireless transmitter configured to transmit wireless signals to a remote haptic actuating device. In this respect, signals from distal portion 16 can be transmitted to the remote device for actuating haptic effects on the user or even on another person. For example, signals can be transmitted to a body-mounted actuator assembly located on the surgeon, such as around the surgeon's wrist, inside the gown, etc. The body-mounted actuator does not necessarily need to be sterile. Wireless transmission in this sense may be for short range communication, such as using Bluetooth® or other similar technology.

Handle portion 12 can provide power to distal portion 16 as needed to power any sensors of distal portion 16. For example, a low voltage, e.g., 5V, may be sufficient to power many sensing elements. In this case, handle portion 12 can include an internal power source, such as, for example, rechargeable batteries. When sensors of distal portion 16 are powered, distal portion 16 can also transmit signals from the respective sensors back to handle portion 12. In response to receiving the feedback signal from distal portion 16, handle portion can process the signals to indicate the results to the user in any suitable manner. For example, handle portion 12 may include a haptic actuator for invoking a haptic effect upon the user. In additional or alternative examples, handle portion 12 may also include a display device for visually displaying results of the sensors of distal portion 16. With a power source contained within handle portion 12, the power source can supply power as needed to the various output devices, e.g., haptic actuators, display devices, etc., maintained with respect to handle portion 12.

In some embodiments, handle portion 12 may also provide a large amount of AC or DC power to distal portion 16. For example, when modular tool 10 is used as a cauterization device, approximately 50 watts of power may be needed to cauterize an organ. With the capability to supply such a high power, modular tool 10 includes proper insulating material to minimize crosstalk or electromagnetic interference of the high power with other electronics. For cauterization, an external power source may be used in conjunction with modular tool 10 to provide a proper amount of power. The external power source in this case may be configured to provide power to distal portion 16 via any suitable connection mechanisms on handle portion 12 and/or interface portion 14.

Distal portion 16 may include any suitable type of tip or end piece for performing any number of functions. For example, regarding surgical tools, distal portion 16 may include a clamp, grasper, forceps, scissors, cautery, tissue identifying probe, tip resistance sensor, trajectory sensor, Doppler sensor, active or passive PZT sensor, PVDF strain gauge, ultrasound detector, blood flow sensor, pulse sensor, temperature sensor, sensor for monitoring other patient vitals, etc. Some examples of non-surgical distal portion 16 elements may include drills, screwdrivers, saws, hammers, etc.

Figure 2A:
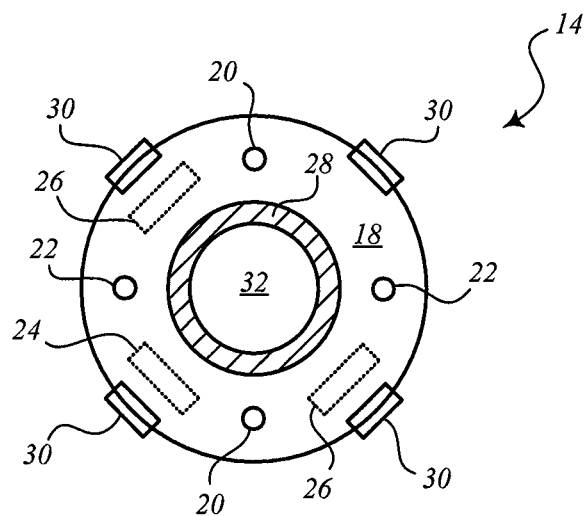
FIGS. 2A and 2B are diagrams illustrating the interface portion shown in FIG. 1 according to one embodiment.
Figure 2B:
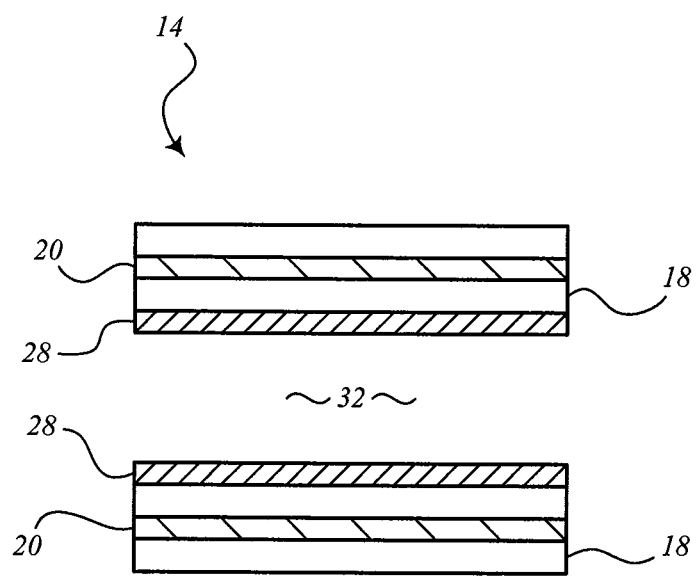

FIGS. 2A and 2B are diagrams of an embodiment of interface portion 14 shown in FIG. 1, where FIG. 2A is an end view of interface portion 14 and FIG. 2B is a cross-sectional side view of interface portion 14. In this embodiment, interface portion 14 includes a substrate 18 containing any suitable material for providing support for the other elements. In some embodiments, substrate 18 is formed having a hollow cylindrical shaft having a length of approximately 2-3 cm and a diameter of approximately 2-3 cm. Interface portion 14 also includes power conductors 20, signal communication conductors 22, a processing device 24, sensors 26, insulating material 28, and latching mechanisms 30. Insulating material 28 forms a layer between substrate 18 and a cylindrical channel 32 formed coaxially with interface portion 14.

In general, interface portion 14 is designed as an adapter to connect to handle portion 12 and distal portion 16 to provide support for forming a relatively rigid modular tool 10 that can be used as designed. Also, interface portion 14 is an electro-mechanical interface device designed to enable mechanical translation and electrical communication between handle portion 12 and distal portion 16. Interface portion 14 allows a mechanical and high voltage electrical connection through channel 32 to distal portion 16. In some embodiments, connection can be made to a laparoscopic tip having standard diameter dimensions of 3 mm, 5 mm, or 10 mm. One of any number of handle portions can be selected for attachment with one of any number of distal portions. Selection of handle portion 12 and distal portion 16 may be based on a surgeon's preference or to support advances in technology of handle portions, interface portions, and/or distal portions. The selected portions can be attached by way of interface portion 14.

Two power conductors 20 are illustrated in FIG. 2, where the potential difference between the two creates an electrical current at the terminating sensor of distal portion 16 that completes the circuit. In some embodiments, however, more than one pair of power conductors can be incorporated in interface portion 14 for supplying power for additional sensors in distal portion 16 and/or for supplying different voltage or current levels as needed by different types of sensors. Similarly, two signal communicating conductors 22 are illustrated in FIG. 2 for creating a circuit along which signals can be transmitted between handle portion 12 and distal portion 16. Power conductors 20, signal communication conductors 22, and any other conductors of interface portion 14 can be embedded in substrate, which can act as an insulator for the conductors. Also, these conductors extend the length of interface portion 14 to transmit signals or power from one end to the other.

Interface portion 14 can include any suitable contact elements for creating an adequate electrical connection between contact elements of the conductors of handle portion 12 and/or distal portion 16 with conductors 20 and 22. For example, the contact elements may include spring contact, corresponding male and female connector contacts, etc. Also, the contact elements and conductors can be used for carrying digital and/or analog signals. Conductors 20 and 22 can be designed to carry low voltage signals compared to the high voltage signals transmitted through channel 32. In some embodiments, the low voltage may be approximately 5V.

Processing device 24 may be a general-purpose or specific-purpose processor or microcontroller, depending on the particular use. In some embodiments, processing device 24 can be implemented using discrete logic circuitry, an application specific integrated circuit (ASIC), a programmable gate array (PGA), a field programmable gate array (FPGA), etc., or any combination thereof.

Sensors 26 may be implemented to detect any number of parameters associated with interface portion 14. Two sensors 26 are shown for illustrative purposes only, but it should be recognized that any number of sensors 26 may be incorporated in interface portion 14 as needed and depending on the particular design. In some embodiments, one or more sensors 26 may be configured as shaft sensors. For example, sensors may include an optical encoder for monitoring shaft position when a shaft of distal portion 16 is inserted into or removed from channel 32. Sensors 26 may also be configured as inductive sensors for monitoring when a high current is flowing through a cautery or other similar high power device inserted in channel 32.

The layer of insulating material 28, positioned between substrate 18 and channel 32, is configured to minimize or eliminate crosstalk or electromagnetic interference of a high power or current flowing through channel 32. For example, when modular tool 10 is configured as a cauterization device or other similar tool in which high power is conducted from handle portion 12 to distal portion 16, insulating material 28 insulates the other conductors, e.g., low voltage conductors 20 and 22, from the high power cautery in channel 32.

In general, latching mechanisms 30 can include any suitable structure and are illustrated in FIG. 2A to merely convey the concept of physically latching interface portion 14 with either or both of handle portion 12 and/or distal portion 16. Latching mechanisms 30 are located on both ends of interface portion 14 for assembling with both handle portion 12 and distal portion 16. Likewise, handle portion 12 and distal portion 16 include compatible latching devices for enabling engagement of portions together. Although four latching mechanisms 30 are shown, it should be recognized that any number of latching mechanisms 30 can be included on each end of interface portion 14. Latching mechanisms 30 can be configured in any suitable manner with any suitable size or shape and can be used to connect the different portions together to form modular tool 10. Latching mechanisms 30 are designed to provide sufficient strength and stability to allow the user of modular tool 10 to easily and effectively perform the intended functions without inadvertent disconnection of the portions during use.

Furthermore, latching mechanisms 30 are designed to properly align the contact elements of the conductors of handle portion 12 and/or distal portion 16 with corresponding contact elements and conductors of interface portion 14. With proper alignment, power conductors of handle portion 12 and distal portion 16 can be connected to power conductors 20 of interface portion 14 to properly supply power as needed. Also, signal communication conductors 22 can properly carry signals between corresponding signal communication conductors of handle portion 12 and distal portion 16. It should be noted that handle portion 12 and distal portion 16 can be designed to include corresponding latching components for engaging latching mechanisms 30 of interface portion 14 to properly latch the portions together.

Channel 32 is designed to allow a mechanical connection between handle portion 12 and distal portion 16. For example, distal portion 16 may include a rod that is inserted through channel 32 and connected to corresponding mechanisms for translating mechanical forces.

Depending on the particular need or design of interface portion 14, more or fewer elements of interface portion 14 may be included. For example, interface portion 14 may further comprise a digital interface for digital communication or integrated sensing. Interface portion 14 may be configured to support different types of shafts and sensors of distal portion 16. Therefore, interface portion 14 may include any suitable shape or design, with differently sized or shaped channels 32 as needed for particular types of shafts and sensors.

Figure 3:
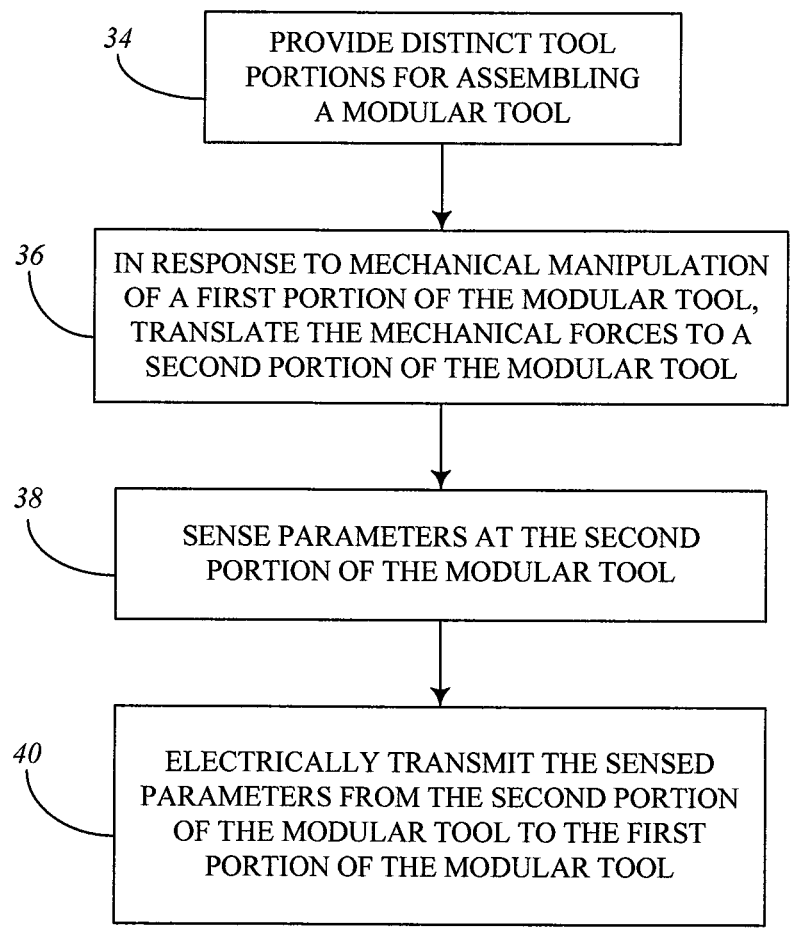
FIG. 3 is a flow diagram of a method of operating a modular tool according to one embodiment.

FIG. 3 is a flow diagram showing an embodiment of a method of operation of a modular tool. In this embodiment, the method comprises providing distinct tool portions that can be assembled into a modular tool, as indicated in block 34. In some embodiments, the modular tool comprises a handle portion and a distal portion, where manipulation of one or more components of the handle portion causes movement of one or more components of the distal portion. According to many embodiments described herein, the method may include providing an interface portion to be assembled with the handle portion and distal portion and positioned between the two other portions. In this respect, interface portion may be used for connected different types of handle portions with different types of distal portions.

As indicated in block 36, the modular tool reacts to forces applied upon the tool, such as forces applied by a user. In response to mechanical manipulation of the first portion, e.g., handle portion, of the modular tool, mechanical forces are translated to a second portion, e.g., distal portion, of the modular tool. As indicated in block 38, one or more parameters are sensed at the second portion of the modular tool. As indicated in block 40, the sensed parameters are electrically transmitted from the second portion of the modular tool to the first portion of the modular tool. In some embodiments, the method of FIG. 3 may further comprise utilizing the signals at the handle portion in any suitable manner. For example, the signals may be used to display the sensed parameters on a display device and/or can be used to actuate haptic effect via a haptic actuating device associated with the handle portion.

Therefore, it should be recognized that the modular tool, which includes portions that can be connected together and can be removed from each other, includes mechanical and electrical communication between the portions of the tool. With such a method, it is possible to interchange any number of handle portions with any number of distal portions of the modular tool. This allows great flexibility with respect to the user's selection of different types of handle portions and distal portions based on preference and/or need. While manipulating the handle portion, causing the distal portion to mechanically react, the distal portion can also sense one or more parameters that can be transmitted back to the handle portion for indicating the sensed parameters to the user. It should be understood that one or more of the steps, processes, and/or operations described herein may be executed substantially simultaneously or in a different order than explicitly described, as would be understood by one of ordinary skill in the art.

The embodiments described herein represent a number of implementation examples and are not intended to necessarily limit the present disclosure to any specific embodiments. Instead, various modifications can be made to these embodiments as would be understood by one of ordinary skill in the art. Any such modifications are intended to be included within the spirit and scope of the present disclosure and protected by the following claims.

We claim:

1. An interface mechanism of a modular laparoscopic hand tool for attachment between a handle portion and a distal portion of the hand tool, the interface mechanism comprising:
    a substrate formed from a cylindrical shaft segment of a rigid material having a length and diameter of substantially equal dimensions and defining a channel therethrough in which a mechanical connection between the handle portion and the distal portion can be made;
    a first latching mechanism configured to latch the shaft segment to the handle portion of the modular laparoscopic hand tool;
    a second latching mechanism configured to latch the shaft segment to the distal portion of the modular laparoscopic hand tool; and
    means for conducting electrical signals from the distal portion to the handle portion through the interface mechanism, wherein the means for conducting electrical signals comprises a pair of electrical conductors embedded in a wall of the shaft segment to be radially spaced from the channel of the shaft segment and that extend the length of the interface mechanism, and
wherein the interface mechanism is an adapter that when connected between the handle portion and the distal portion provides support for forming the rigid modular laparoscopic hand tool.

2. The interface mechanism of claim 1, wherein movement of one or more components of the handle portion causes movement of one or more components of the distal portion via the mechanical connection.

3. The interface mechanism of claim 1, further comprising a shaft sensor configured to detect the presence of a shaft of the distal portion when the shaft is inserted in the channel.

4. The interface mechanism of claim 1, further comprising a layer of insulating material positioned between the shaft segment and the channel, wherein the insulating material is configured to minimize electromagnetic interference from high electrical power flowing through the channel.

5. The interface mechanism of claim 1, further comprising means for supplying power from the handle portion to the distal portion.

6. The interface mechanism of claim 5, wherein the means for supplying power comprises a pair of electrical conductors embedded in the wall of the shaft segment and running the length of the interface mechanism.

7. A modular laparoscopic hand tool comprising:
    a handle portion configured to be manipulated by a user; and a distal portion configured to be attached to the handle portion, the distal portion further configured to be removable from the handle portion by the user; and the interface mechanism as described in claim 1, wherein manipulation of the handle portion causes movement of one or more components of the distal portion; and wherein the distal portion is further configured to sense one or more physical properties and to transmit the sensed physical properties to the handle portion.

8. The modular laparoscopic hand tool of claim 7, wherein the interface mechanism enables the user to attach different types of handle portions with different types of distal portions.

9. The modular laparoscopic hand tool of claim 8, wherein the interface mechanism is configured to translate mechanical forces between the handle portion and the distal portion.

10. The modular laparoscopic hand tool of claim 8, wherein the interface mechanism is configured to communicate electrical signals between the handle portion and the distal portion.

11. The modular laparoscopic hand tool of claim 10, wherein the handle portion is configured to supply a relatively small voltage to the distal portion to power one or more sensors of the distal portion that are configured to sense the one or more physical properties.

12. The modular laparoscopic hand tool of claim 10, wherein the handle portion is configured to supply a relatively high voltage to the distal portion.

13. The modular laparoscopic hand tool of claim 12, wherein the distal portion is configured to use the high voltage for cauterization.

14. The modular laparoscopic hand tool of claim 7, wherein the handle portion comprises a wireless transmission device for wirelessly communicating the sensed physical properties to a remote device.

15. The modular laparoscopic hand tool of claim 7, wherein the handle portion is reusable and the distal portion is disposable, and wherein the distal portion can be removed from the handle portion after use and discarded.

16. The modular laparoscopic hand tool of claim 7, wherein the handle portion comprises a haptic actuator configured to invoke a haptic effect on the user in response to the signals transmitted from the distal portion.

17. The modular laparoscopic hand tool of claim 7, wherein the handle portion comprises a display device configured to display a value of the one or more sensed physical properties.

* * * * *